(12) United States Patent
Lu et al.

(10) Patent No.: US 12,109,362 B1
(45) Date of Patent: Oct. 8, 2024

(54) NASAL BREATHING AND VENTILATION DEVICE

(71) Applicant: GUANGDONG JIUCCO MEDICAL EQUIPMENT CO., LTD., Guangdong (CN)

(72) Inventors: Hua Lu, Guangdong (CN); Jiejing Lu, Guangdong (CN)

(73) Assignee: GUANGDONG JIUCCO MEDICAL EQUIPMENT CO., LTD., Guangdong (CN)

( * ) Notice: Subject to any disclaimer, the term of this patent is extended or adjusted under 35 U.S.C. 154(b) by 0 days.

(21) Appl. No.: 18/702,802

(22) PCT Filed: Nov. 10, 2022

(86) PCT No.: PCT/CN2022/131188
§ 371 (c)(1),
(2) Date: Apr. 19, 2024

(87) PCT Pub. No.: WO2023/083268
PCT Pub. Date: May 19, 2023

(30) Foreign Application Priority Data

Nov. 12, 2021 (CN) .......................... 202111339319.3

(51) Int. Cl.
*A61M 16/06* (2006.01)
(52) U.S. Cl.
CPC ................ *A61M 16/0616* (2014.02)
(58) Field of Classification Search
CPC ......... A61F 5/08; A61F 5/56; A61M 16/0003; A61M 16/0057; A61M 16/0069;
(Continued)

(56) References Cited

U.S. PATENT DOCUMENTS 2,663,297 A * 12/1953 Turnberg .......... A61M 16/0666
D27/135
4,944,310 A * 7/1990 Sullivan ............ A61M 16/0683
128/207.18
(Continued)

FOREIGN PATENT DOCUMENTS

CN 201120028 9/2008
CN 110354352 10/2019
(Continued)

OTHER PUBLICATIONS

"International Search Report (Form PCT/ISA/210) of PCT/CN2022/131188", mailed on Feb. 7, 2023, with English translation thereof, pp. 1-4.

*Primary Examiner* — Annette Dixon
(74) *Attorney, Agent, or Firm* — JCIPRNET

(57) ABSTRACT

A nasal breathing and ventilation device, includes ventilation tubes. One end of each ventilation tube is provided with a nasal dilator. Each nasal dilator includes a nasal dilator channel and a plurality of dilator rings. One end of each nasal dilator channel is provided with a through hole. Each nasal dilator is supported and fixed in the nasal cavity by means of the dilator rings thereof, and is not easy to fall out. The end of each nasal dilator channel away from the through hole is in communication with each ventilation tube. The tube wall at the end of each ventilation tube close to the nasal dilator is provided with ventilation holes. The end of each (Continued)

ventilation tube away from the nasal dilator is connected to a ventilator, and the ventilator conveys air into the nasal cavity at a certain pressure.

2 Claims, 3 Drawing Sheets

(58) Field of Classification Search
CPC ............ A61M 16/0096; A61M 16/024; A61M 16/0493; A61M 16/06; A61M 16/0605; A61M 16/0611; A61M 16/0616; A61M 16/0633; A61M 16/0666; A61M 16/0672; A61M 16/0677; A61M 16/0683; A61M 16/08; A61M 16/0816; A61M 16/0825; A61M 16/0833; A61M 16/0858; A61M 16/0875; A61M 16/1075; A61M 16/109; A61M 16/12; A61M 16/125; A61M 16/127; A61M 16/16; A61M 16/20; A61M 16/206; A61M 2016/0024; A61M 2016/0027; A61M 2016/0661; A61M 2016/1025; A61M 2202/0208; A61M 2205/0216; A61M 2205/3331; A61M 2210/0618; A61M 2210/0625; Y10T 29/49826

See application file for complete search history.

(56) References Cited

U.S. PATENT DOCUMENTS

| | | | |
|---|---|---|---|
| 6,484,725 B1* | 11/2002 | Chi | A63B 23/18 |
| | | | 128/207.18 |
| 2005/0011524 A1* | 1/2005 | Thomlinson | A61M 16/0825 |
| | | | 128/207.18 |
| 2005/0028822 A1 | 2/2005 | Sleeper et al. | |
| 2006/0107958 A1 | 5/2006 | Sleeper | |
| 2008/0276938 A1 | 11/2008 | Jeppesen et al. | |
| 2009/0101154 A1* | 4/2009 | Mutti | A61M 16/0666 |
| | | | 128/207.18 |
| 2010/0037897 A1* | 2/2010 | Wood | A61M 16/0683 |
| | | | 128/207.11 |
| 2010/0331777 A1* | 12/2010 | Danielsson | A62B 23/06 |
| | | | 606/199 |
| 2012/0138060 A1* | 6/2012 | Barlow | A61M 16/0688 |
| | | | 128/205.25 |
| 2016/0175548 A1 | 6/2016 | Spence et al. | |
| 2016/0317773 A1* | 11/2016 | Buddharaju | A61M 25/02 |
| 2017/0119987 A1 | 5/2017 | Buddharaju | |
| 2017/0224942 A1* | 8/2017 | Barbour | A61M 16/06 |

FOREIGN PATENT DOCUMENTS

| | | |
|---|---|---|
| CN | 211157990 | 8/2020 |
| CN | 113769224 | 12/2021 |

* cited by examiner

NASAL BREATHING AND VENTILATION DEVICE

CROSS-REFERENCE TO RELATED APPLICATION

This application is a 371 of international application of PCT application serial no. PCT/CN2022/131188, filed on Nov. 10, 2022 which claims the priority benefit of China application no. 202111339319.3, filed on Nov. 12, 2021. The entirety of each of the above-mentioned patent applications is hereby incorporated by reference herein and made a part of this specification.

TECHNICAL FIELD

The present invention relates to the technical field of ventilator devices, and in particular to, a nasal breathing and ventilation device.

BACKGROUND

Since the outbreak of the COVID-19 pandemic, there has been an increased demand for ventilators, and the demand for ventilation masks used in conjunction with ventilators has also risen. Ventilators are used clinically to treat respiratory difficulties caused by the novel coronavirus, primary or secondary lung diseases, and related conditions. Currently, the respiratory masks typically used in conjunction with ventilators are headband-style respiratory masks.

In many situations, it is inconvenient to use headband-style respiratory masks, which are likely to have adverse effects on patients. For example, when wearing a headband-style respiratory mask, a patient with head injury may have the wound infected. It is neither friendly for the patient who has low tolerance for ventilator treatment, or suffers from claustrophobia and thus is unaccustomed to wearing a headband-style respiratory mask. Additionally, it is uncomfortable for some clinical patients, who experience respiratory sleep apnea or hypopnea syndrome, to wear the headband-style respiratory mask during sleep, making it difficult for them to fall asleep.

In the related art, a nasal cannula mask for ventilation control is provided in a form of three ports for tubing. One port is connected to the tubing connector of the ventilator while the other two ports are inserted into the patient's two nostrils to seal them. As a result, the respiratory airflow can enter the nasopharynx via the nasal cannulae while simultaneously sealing the mouth to prevent air leakage through the oral cavity. However, the ventilation mask disclosed in this scheme is not effectively fixed and likely to fall off when the patient breathes. Especially, the patient is likely to accidentally touch the ventilation mask when sleeping.

Furthermore, some medical nasal masks are provided for basically meeting the requirements of the use of anaesthesia. Due to the extremely low airflow pressure as one use condition of anaesthesia, no high demands are imposed on the stability of fixing the nasal mask and on the air flowability. However, under the airflow pressure provided by the ventilator, there is a specified requirement for stability of the nasal cannula structure. As a result, this type of nasal mask cannot meet the requirements for use of ventilators.

SUMMARY

To overcome the defects of the headband-style respiratory masks, the present invention provides a nasal breathing and ventilation device, which is mainly in cooperation with the ventilator for use. The ventilation device is effectively fixed in inpatient's nasal cavity while providing assisted ventilation, helping the patient to breathe, addressing the shortcomings of headband-style respiratory masks, and ensuring the stability of the nasal cannula structure.

To resolve the foregoing technical problem, the present invention uses the following technical solution:

A nasal breathing and ventilation device is provided, including a ventilation tube, where one end of the ventilation tube is provided with a nasal brace, the nasal brace includes a nasal brace channel and multiple support rings. One end of the nasal brace channel is provided with a through hole, and the through hole is formed by multiple air holes. The support rings are disposed on a circumferential outer wall of the nasal brace channel, sequentially arranged along a direction of the nasal brace channel, and configured to support a nasal-cavity inner wall. The support rings are co-axially arranged. The support ring at one end away from the through hole is a maximum outer diameter-support ring, and along a nasal insertion direction of the nasal brace, outer diameters of the support rings are decreased sequentially. The nasal brace is supported by its support rings to be fixed in the nasal cavity and less likely to fall off. During use, the nasal brace structure is inserted into the patient's nasal cavity, and the support rings on the outer periphery of the nasal brace adapt to the size of the nasal cavity and snugly adhere to and provide support against the inner wall of the nasal cavity, ensuring effective fixing without additional headband. This makes the ventilation device simple and convenient, and does not affect the use by patients with head injuries. According to the structure of the human nasal cavity, the nasal brace is designed to gradually decrease in size along the nasal insertion direction, ensuring better comfort for the patient during use. Therefore, the outer diameters of the support rings gradually decrease, with the maximum outer diameter-support ring primarily providing limitation, making the nasal brace stuck in the nasal cavity.

The ventilation function of the ventilation tube does not interfere with the support function of the nasal brace, and can ensure smooth ventilation. The ventilation tube is connected to the ventilator, such that the ventilator delivers air into the nasal cavity at a specific pressure. The nasal brace channel is equivalent to an extension of the ventilation tube in the nasal cavity, so as to complete ventilation in the ventilation tube via the through holes at an end of the nasal brace channel.

In addition, one end of the nasal brace channel away from a through hole communicates with the ventilation tube; and a tube wall at one end of the ventilation tube close to the nasal brace is provided with multiple exhaust holes, where the exhaust hole communicates with an inner wall and an outer wall of the ventilation tube, an opening of the exhaust hole on a side of the inner wall is close to the nasal brace, and an opening of the exhaust hole on a side of the outer wall is away from the nasal brace.

When the ventilator delivers air into the nasal cavity at a specific pressure, the support stability of the nasal brace should be ensured, and then the patient's spontaneous respiratory gas exchange should not be affected. Thus, the exhaust holes are primarily used for exchange of the patient's respiratory gases and the discharge of exchanging gases such as carbon dioxide, with the ventilation direction arranged to facilitate the exhausting. The opening of the exhaust hole on a side of the inner wall is close to the nasal brace and the opening of the exhaust hole on a side of the outer wall is away from the nasal brace. Through such arrangement, the fresh airflow is uneasy to leak outside via the exhaust hole during air delivery, and during air exhaust, in response to the airflow pressure change of the ventilator, the exchanged airflow is easy to exhaust via the exhaust holes.

As a preferred solution, the nasal brace is detachably connected to the end portion of the ventilation tube. To ensure hygiene, nasal braces are typically disposable, allowing for prompt replacement. Therefore, the nasal brace and the end portion of the ventilation tube can be quickly assembled and disassembled. In addition, the nasal brace may further be not connected to the ventilation tube and used alone. The nasal brace is fixed in the nasal cavity, and the nasal brace channel is used for ventilation into the nasal cavity or another therapeutic approach.

In a preferred solution, the nasal brace is fitted onto an end portion of the ventilation tube, with an assembly relationship being clearance fit or interference fit. The connection between the nasal brace and the ventilation tube may be threaded connection, clamping, or the like. Preferably, the connection is fitting, and in order to ensure air-tightness, the parts to be assembled are in clearance fit or interference fit.

In a preferred solution, such two ventilation tubes are combined for use, arranged in parallel, and provided with a connecting structure therebetween. The ventilation tube may be used alone, or combined with another one for use. The nasal braces of the ventilation tubes on two sides are respectively inserted into the patient's nasal cavities and fixed for ventilation. When two ventilation tubes are used together, they can be fixed using the connecting structure, so as not to be twined.

Preferably, the connecting structure is a Velcro connecting structure, a button connecting structure, a buckle connecting structure, or a hook connecting structure. The connecting structure includes two parts, respectively connecting tube bodies of the ventilation tubes on two sides, and the two parts are connected and fixed by means of Velcro, a button, a snap, a buckle, or the like.

In a preferred solution, the two ventilation tubes are each provided with a nasal wing, and the nasal wings open outward and are configured to respectively grip two external sides of a nose. The nasal wings are configured to assist in fixing. After the nasal braces are inserted into the nasal cavities, the nasal wings on two sides grip external sides of the nose for further fixing, preventing the ventilation tubes from falling off due to significant movement.

In a preferred solution, the nasal breathing and ventilator further includes a ventilation box, where each ventilation tube communicates with the ventilation box and is connected to a ventilator via the ventilation box; and the ventilation box is provided with a backup interface. The ventilation tube is detachably connected to the ventilation box, such that the ventilator delivers air. The backup interface can be used for connecting another device, such as an oxygen delivery device for anesthesia or the like.

Generally, the material of the support rings is elastic plastic. To ensure the comfort after the support rings are inserted into the nose, the support rings are typically made of a soft silicone material that does not harm the inner walls of the nasal cavities.

Compared with the related art, the present invention discloses a nasal breathing and ventilation device, with the following beneficial effects: The ventilation device has a simple and reasonable structure, and, with the support in the nasal cavities, is specifically suitable for patients with head injuries, and patients who have low tolerance for ventilator treatment, or suffer from claustrophobia and thus are unaccustomed to wearing a headband-style mask. In addition, the ventilation device may use a single ventilation tube in a case that a nasal cavity is blocked, or combine two ventilation tubes for use in the entire nose. Through such ventilation tubes, the ventilator delivers air into the nasal cavities at a specified pressure, helping to alleviate sleep apnea or hypopnea syndrome, and other respiratory difficulties.

DETAILED DESCRIPTION OF EMBODIMENTS

Figure 1:
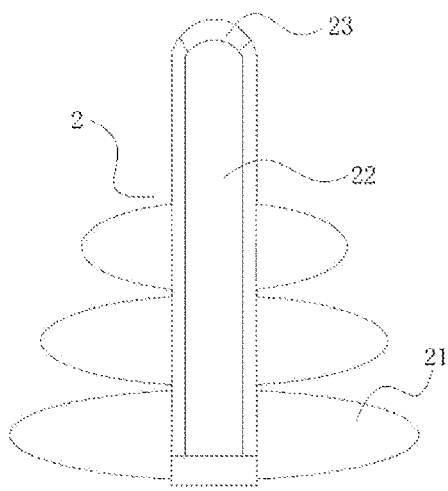
FIG. 1 is a schematic structural diagram according to Embodiment 1.

The accompanying drawings are provided for illustrative purposes only and should not be construed as limitation on the scope of this application. To better illustrate the embodiments, some components in the drawings may be omitted, enlarged, or reduced, which does not necessarily represent the actual product dimensions. It is understandable for those skilled in the art that some known structures and their descriptions in the drawings may be omitted. The positional relationships described in the drawings are provided for illustrative purposes only and should not be construed as limiting the scope of this application.

The technical solutions of the present invention are further described specifically with reference to drawings based on specific embodiments.

Embodiment 1

Figure 2:
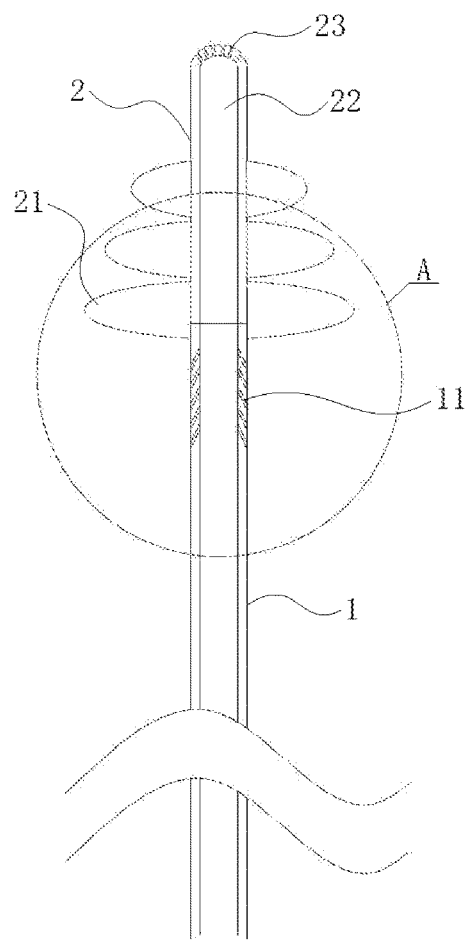
FIG. 2 is a schematic structural diagram according to Embodiment 1.

As shown in FIGS. 1 and 2, this embodiment provides a nasal breathing and ventilation device, including a ventilation tube 1. One end of the ventilation tube 1 is provided with a nasal brace 2, and the other end is connected to the ventilator. The ventilation tube 1 is typically made of medical-grade non-toxic transparent soft polyvinyl chloride (PVC) plastic or high-performance thermoplastic elastomer (TPE) material.

Specifically, the nasal brace 2 includes a nasal brace channel 22 and a plurality of support rings 21, and one end of the nasal brace channel 22 is provided with a through hole 23. Specifically, the support rings 21 are disposed on a circumferential outer wall of the nasal brace channel 22 and sequentially arranged along a direction of the nasal brace channel 22. The nasal brace 2 is supported by the support rings 21 to be well fixed on the nasal-cavity inner wall, and thus is unlikely to fall off.

In this embodiment, the support rings are arranged co-axially, with the support ring 21 at one end away from the through hole 23 being the maximum outer diameter-support ring. Specifically, in order to adapt to the structure of the human nasal cavity, the outer diameters of the support rings 21 are sequentially decreased along the nasal insertion direction of the nasal brace 2, ensuring good comfort when the support rings are inserted into the nasal cavity. In addition, the support ring 21 is made of an elastic plastic material, such as soft silicone, which is less likely to harm the inner wall of the nasal cavity. The maximum outer diameter-support ring serves as a limit ring to be stuck in the nasal cavity, preventing over-insertion of the nasal brace 2. During use, the nasal brace 2 is inserted into human nasal cavity. In addition, the nasal brace may further be not connected to the ventilation tube and used alone. The nasal brace is fixed in the nasal cavity, and the nasal brace channel is used for ventilation into the nasal cavity or another therapeutic approach.

During wearing, the nasal brace 2 is inserted into the patient's nasal cavity, and the support rings 21 support the inner wall of the nasal cavity for effective fixing without additional headband. The ventilation device especially does not affect the use by patients with head injuries, and thus has large use coverage.

In this embodiment, the nasal brace 2 is detachably connected to the end portion of the ventilation tube 1. During actual application, the nasal brace and the ventilation tube may be integrally produced. In addition, the nasal brace 2 is provided with a nasal brace channel 22 in communication with the ventilation tube 1, and the support rings 21 are arranged along the outer circumference of the nasal brace channel 22. In addition, the through hole 23 at one end of the nasal brace channel 22 away from the ventilation tube 1 is formed by multiple air holes. The ventilator delivers air into the nasal cavity via a ventilation tube 1, the nasal brace channel 22, and the through hole 23, helping patients to breathe.

To ensure hygiene, nasal braces 2 are typically disposable, allowing for prompt replacement. Therefore, the nasal brace 2 is quickly assembled with or disassembled from the end portion of the ventilation tube 1 through fitting, for example, interference fit, thus ensuring the air-tightness, and preventing easy falling off.

Figure 3:
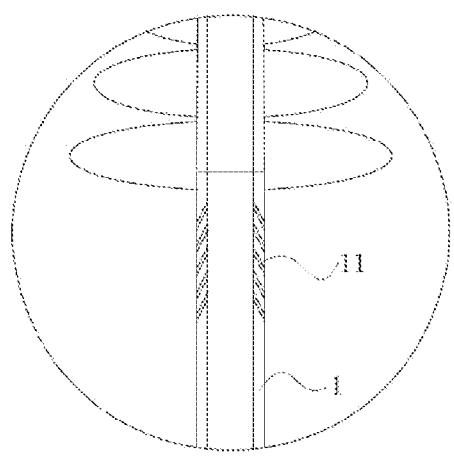
FIG. 3 is a partially enlarged view of position A in FIG. 2.

When the ventilator delivers air into the nasal cavity at a specific pressure, the support stability of the nasal brace should be ensured, and then exchange of the patient's independent respiratory gases should not be affected. Therefore, a tube wall at one end of the ventilation tube 1 close to the nasal brace 2 is provided with multiple exhaust holes 11, where the exhaust hole 11 communicates with an inner wall and an outer wall of the ventilation tube 1, an opening of the exhaust hole 11 on a side of the inner wall is close to the nasal brace 2, and an opening of the exhaust hole 11 on a side of the outer wall is away from the nasal brace 2. The exhaust holes 11 are primarily used for gas exchange and the expulsion of gases such as carbon dioxide when the patient breathes. The fresh airflow is uneasy to leak outside via the exhaust hole 11 during air delivery, and during air exhaust, in response to the airflow pressure change of the ventilator, the exchanged airflow is easy to exhaust via the exhaust holes 11. Thus, the opening of the exhaust hole 11 on a side of the inner wall is arranged close to the nasal brace 2 and the opening of the exhaust hole 11 on a side of the outer wall is away from the nasal brace 2, as shown in FIG. 3.

One end of the ventilation tube 1 is connected to the ventilator, and the airflow passes through the ventilation tube 1 and the nasal brace 2 into the patient's nasal cavity. After the patient completes an inhalation, the ventilator is triggered by a sensor to reduce the oxygen supply, and, in coordination with the patient, expel the exhaled gas reversely from the through hole 23 to the nasal brace 2, and exhaust it through the exhaust hole 11 on the ventilation tube 1. After the patient completes an exhalation, the sensor triggers the ventilator to resume the oxygen supply.

Embodiment 2

Figure 4:
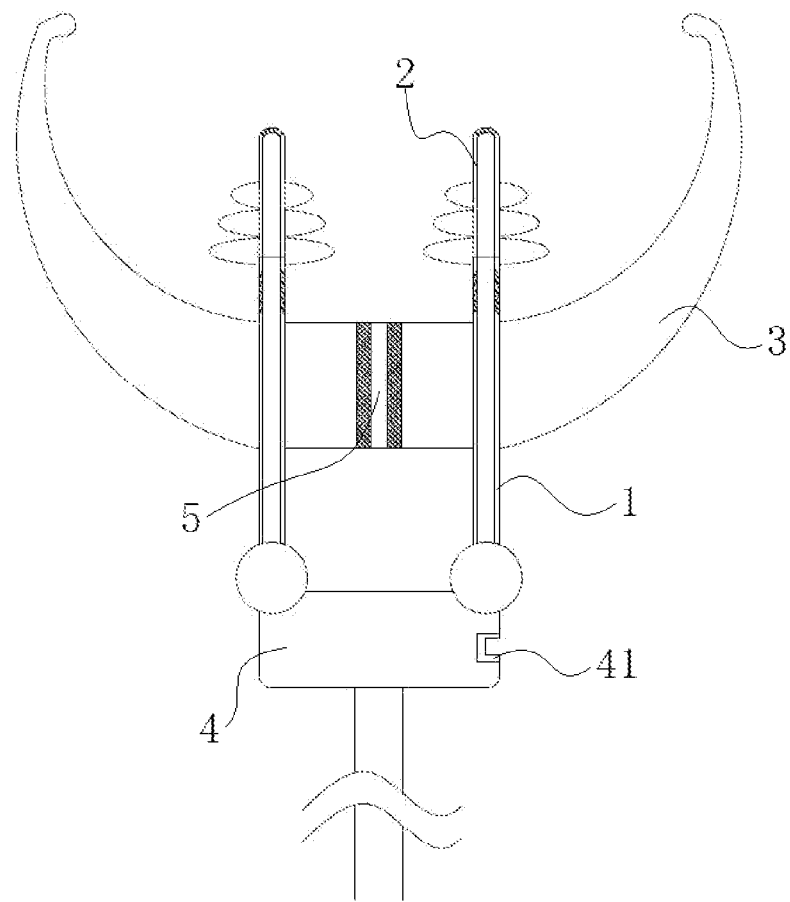
FIG. 4 is a schematic structural diagram according to Embodiment 2.

As shown in FIG. 4, similarly, this embodiment also provides a nasal breathing and ventilation device, including two ventilation tubes 1 combined for use. The structure and operation principle of a single ventilation tube 1 are the same as these in Embodiment 1, with the difference that the two ventilation tubes 1 in this embodiment are arranged in parallel and provided with a connecting structure 5 therebetween. The nasal braces 2 of the ventilation tubes 1 on two sides are respectively inserted into the patient's nasal cavities and fixed for ventilation. When two ventilation tubes 1 are used together, they can be fixed using the connecting structure 5, so as not to be twined.

Specifically, the connecting structure 5 is a Velcro connecting structure. The Velcro connecting structure includes two parts, that is, a Velcro loop material attached to the ventilation tube 1 on one side, and a Velcro hook material attached to the ventilation tube 1 on the other side. Through the attachment between the Velcro loop and hook materials, the two ventilation tubes 1 can be fixed.

The two ventilation tubes 1 are each provided with a nasal wing 3 assisting in fixing. The two nasal wings 3 open outward and respectively grip two external sides of a nose. After the nasal braces 2 are inserted into the nasal cavities, the nasal wings 3 on two sides grip external sides of the nose, preventing the ventilation tubes 1 from falling off due to significant movement.

This embodiment further includes a ventilation box 4. Each ventilation tube 1 communicates with the ventilation box 4 and is connected to the ventilator via the ventilation box 4. The ventilation tube 1 is detachably connected to the ventilation box 4. The ventilation box 4 is a commonly used component in this field, so its structure is not explained in detail herein. It should be noted that this ventilation box 4 is provided with a backup interface 41. The backup interface 41 can be used for connecting another device, such as an oxygen delivery device for anesthesia or the like, which performs delivery using the ventilation device.

Embodiment 3

Figure 5:
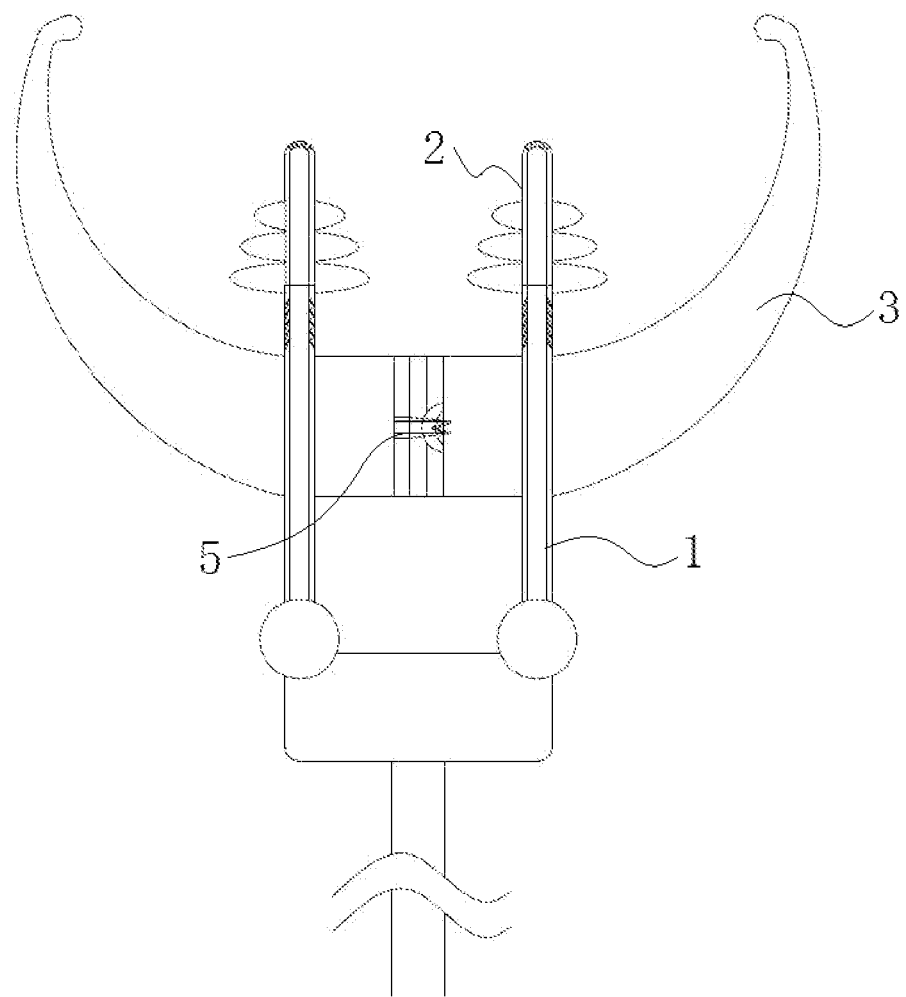
FIG. 5 is a schematic structural diagram according to Embodiment 3.

As shown in FIG. 5, this embodiment also provides a nasal breathing and ventilation device, which has a structure similar to that in Embodiment 2, with the difference that the connecting structure 5 in this embodiment is a hook connecting structure, including two parts, that is, a hook disposed on the ventilation tube 1 on one side and a ring disposed on the ventilation tube 1 on the other side. Through the cooperation between the hood and the ring, the ventilation tubes 1 on two sides can be fixed. Specifically, the hook and the ring are typically connected on the ventilation tubes 1 via a plastic member or a fabric material.

Clearly, the above embodiments of the present invention are provided solely for illustrating the examples of the present invention and should not be considered as limitation on the implementation of the invention. For ordinary skilled persons in this field, additional changes or modifications in different forms can be made based on the above description. It is neither necessary nor feasible to exhaustively enumerate all possible embodiments herein. Any modification, equivalent replacement, improvement, or the like made within the spirit and principle of the present invention shall fall within the protection scope of the claims of the present invention.

The invention claimed is:

1. A nasal breathing and ventilation device, comprising at least one ventilation tube and a ventilation box, wherein one end of the ventilation tube is provided with a nasal brace, the nasal brace comprises a nasal brace channel and a plurality of support rings, one end of the nasal brace channel is provided with a through hole, and the through hole is formed by a plurality of air holes, the ventilation tube is connected to the ventilator, the ventilator delivers air into a nasal-cavity at a specific pressure, the nasal brace channel is an extension of the ventilation tube in the nasal-cavity, the ventilation tube delivers air via the through hole at the one end of the nasal brace channel, the nasal brace is detachably connected to an end portion of the ventilation tube, so as to replace in time, or the nasal brace is used alone without being connected to the ventilation tube, the nasal brace is fixed to the nasal-cavity to deliver air to the nasal-cavity or process other treatment through the nasal brace channel;

the support rings are disposed on a circumferential outer wall of the nasal brace channel, sequentially arranged along a direction of the nasal brace channel, and configured to support a nasal-cavity inner wall to fix the nasal breathing and ventilation device by using the support ring of the nasal brace to replace a head belt; and the support rings are co-axially arranged, the support ring at one end away from the through hole is a maximum outer diameter-support ring, and along a nasal insertion direction of the nasal brace, outer diameters of the support rings are decreased sequentially, the maximum outer diameter-support ring is used for a position limiting ring blocking in a nasal-cavity hole to prevent the nasal brace from overstuffing;

one end of the nasal brace channel away from the through hole is connected to the ventilation tube; and a tube wall at the one end of the ventilation tube close to the nasal brace is provided with a plurality of exhaust holes, wherein the exhaust hole communicates with an inner wall and an outer wall of the ventilation tube, an opening of the exhaust hole on a side of the inner wall is close to the nasal brace, and an opening of the exhaust hole on a side of the outer wall is away from the nasal brace, after a patient completes an inhalation, the ventilator is triggered by a sensor to reduce an oxygen supply, and, in coordination with the patient, expel an exhaled gas reversely from the through hole to the nasal brace, and exhaust it through the exhaust hole on the ventilation tube, after the patient completes an exhalation, the sensor triggers the ventilator to resume the oxygen supply, the at least one ventilation tube comprises two ventilation tubes combined for use, arranged in parallel, and provided with a connecting structure therebetween, the two ventilation tubes are each provided with a nasal wing, and the nasal wings open outward and are configured to respectively grip two external sides of a nose, the ventilation tubes are respectively used or combined for use, the ventilation tubes are fixed by the connecting structure when the ventilation tubes are used at the same time to prevent the ventilation tubes from twining, each of the ventilation tubes communicates with the ventilation box and is connected to a ventilator via the ventilation box; and the ventilation box is provided with a backup interface.

2. The nasal breathing and ventilation device according to claim 1, wherein the nasal brace is fitted onto an end portion of the ventilation tube, with an assembly relationship being clearance fit or interference fit.

* * * * *